United States Patent [19]
Confer et al.

[11] Patent Number: 6,166,062
[45] Date of Patent: Dec. 26, 2000

[54] PHARMACEUTICAL COMPOSITIONS CONTAINING PHOSPHOLIPASE INHIBITOR

[75] Inventors: William Lester Confer, Indianapolis, Ind.; Hideaki Tai, Osaka, Japan

[73] Assignees: Shionogi & Co., Ltd., Osaka, Japan; Eli Lilly and Company, Indianapolis, Ind.

[21] Appl. No.: 09/260,490

[22] Filed: Mar. 2, 1999

Related U.S. Application Data

[60] Provisional application No. 60/076,659, Mar. 3, 1998.
[51] Int. Cl.[7] .......................... A61K 31/40; A61K 31/405
[52] U.S. Cl. ............................................. 514/419; 514/415
[58] Field of Search ....................... 514/419, 415

[56] References Cited

U.S. PATENT DOCUMENTS 5,654,326  8/1997  Bach et al. ............................... 514/419

FOREIGN PATENT DOCUMENTS 0 675 110  10/1995  European Pat. Off. .

OTHER PUBLICATIONS

Dr. Fiedler, Lexikon Der Hilfsstoffe Für Pharmazie, Kosmetik Und Angrenzende Gebiete, Bd. 1, pp. 309–311 (1989) Editio Cantor, Aulendorf, Germany (no translation).
Dr. Fiedler, Lexikon Der Hilfsstoffe Für Pharmazie, Kosmetik Und Angrenzende Gebiete, Bd. 2, pp. 751–755 (1989) Editio Cantor, Aulendorf, Germany (no translation).

*Primary Examiner*—William R. A. Jarvis
*Attorney, Agent, or Firm*—Foley & Lardner

[57] ABSTRACT

A lyophilized pharmaceutical composition is described which contains Sodium [[3-(2-amino-1,2-dioxoethyl)-2-ethyl-1-phenylmethyl)-1H-indol-4-yl]oxy]acetate, a Solubilizer, and a Stabilizer. Such compositions are storage stable and readily dissolve in aqueous medium to give injectable solution for treatment of sepsis, etc.

24 Claims, No Drawings

PHARMACEUTICAL COMPOSITIONS CONTAINING PHOSPHOLIPASE INHIBITOR

This application claims priority to provisional application No. 60/076,659, filed Mar. 3, 1998.

FIELD OF THE INVENTION

This invention relates to pharmaceutical compositions containing a phospholipase inhibitor, more particularly, to a more stable pharmaceutical composition which contains sodium [[3-(2-amino-1,2-dioxoethyl)-2-ethyl-1-(phenylmethyl)-1H-indol-4-yl]oxy]acetate as an active ingredient.

BACKGROUND

Sodium [[3-(2-amino-1,2-dioxoethyl)-2-ethyl-1-(phenylmethyl)-1H-indol-4-yl]oxy]acetate (hereinafter referred to as Compound (I) or Active Ingredient in this specification) is a useful compound as an inhibitor against human non-pancreatic secretory phospholipase A2 (hereinafter referred to as sPLA2), as disclosed in JP-A 7-285933, European Patent Application No. 95302166.4 (EP Publ. No. 0 675 110 A1) and U.S. Pat. No. 5,654,326; the disclosures of which are incorporated herein by reference.

Medicaments for injections are usually formulated into not only emulsions, suspensions or solutions, but also lyophilized preparations to be dissolved before use which are stable, can be preserved and are easily reconstituted. As is generally known to those skilled in the art, it is easy to keep the lyophilized preparations sterile and eliminate foreign insoluble matter from the lyophilized preparations.

Concerning injectable preparations, JP-A 7-285933 discloses an isotonic saline solution of Compound (I) at a concentration of 0.1 g/L and a method to intravenously infuse the saline solution but does not disclose any compositions like those of the present invention. A stable pharmaceutical preparation of Compound (I), in particular, a stable injectable preparation of Compound (I) or a lyophilized preparation of Compound (I) for preparing injectable preparations has long been desired.

Storage of a pharmaceutical composition of Compound (I) prepared by known methods may lead to degradation of its content and a coloring and a worsening of its reconstitution properties, especially in the case of injections to be dissolved before use. It is difficult to provide a pharmaceutical composition of Compound (I) which has good stability and a good reconstitution property, especially for injections of Compound (I) to be dissolved before use, after long storage at room temperature. In more detail, as Compound (I) is a sparingly soluble compound, it is difficult to obtain a clear solution of Compound (I) by only mixing the Compound (I) with a solvent, which makes it desirable to obtain an injection solution and a processing solution.

Even if a clear solution of Compound (I) were obtained by changing conditions such as temperature and the like, degradation of a solution of Compound (I) and a clouding would occur after long storage, resulting in degradation and non-uniform contents of Compound (I) in the solution or the lyophilized injectable preparation of Compound (I). One of the problems to be solved by the present invention is to keep Compound (I) stable in aqueous carriers.

Preparing lyophilized products by the methods of the prior art sometimes causes problems in quality. These problems include a sublimation of some ingredients coinciding with that of water, content of ingredients decreases in the lyophilized product, a partial solidifying of product, lyophilized preparations are cracked and shrunk and may have a thin layer on the top of the cake, adherence to the upper portion of vials and spatters, and non-uniform appearance of lyophilized cakes. Pharmacists and the like require injections to be dissolved in an infusion solution before use, for example, a lyophilized injection should have good reconstitution properties.

Another problem to be solved by the present invention is to provide an excellent lyophilized preparation of Compound (I) of good quality with a uniform appearance, good reconstitution and no degradation of its contents during storage.

SUMMARY

The inventors of the present invention studied various additive agents for preparations of Compound (I) to solve the problems mentioned above. As a result, by adding a Solubilizer, preferably together with a Stabilizer, in a preparation with Compound (I), the present inventors discovered improved preparations of Compound (I) having desired qualities such as no degradation of the contents, good stability, a uniform appearance and a good reconstitution property.

This invention is a storage stable solid lyophilized composition of Compound (I) suitable for making a liquid useful for treatment of Inflammatory Diseases (including sepsis) in mammals.

This invention is also an aqueous solution of a lyophilized composition of Compound (I) useful for the treatment of Inflammatory Diseases (including sepsis) in mammals.

This invention is also a method of making a storage stable and easily reconstituted lyophilized composition of Compound (I).

This invention is also an improved method of treating Inflammatory Diseases in mammals using the lyophilized composition of Compound (I).

This invention is also a unit dosage IV bag or bottle containing a lyophilized composition of Compound (I) dissolved in aqueous medium at a concentration suitable for direct injection into a mammal for treatment of Inflammatory Diseases (including sepsis).

This invention is a dose-concentrate sealed container containing a solid lyophilized composition of Compound (I).

DETAILED DESCRIPTION

Definitions:

The term, "lyophilized composition(s)" refers to the solid freeze-dried composition of matter prepared by the process of this invention and comprising as essential ingredients: (1) sodium [[3-(2-amino-1,2-dioxoethyl)-2-ethyl-1-(phenylmethyl)-1H-indol-4-yl]oxy]acetate; (2) a Solubilizer; and (3) a Stabilizer.

The term, "Active Ingredient" (also called "Compound (I)") refers to the compound, sodium [[3-(2-amino-1,2-dioxoethyl)-2-ethyl-1-(phenylmethyl)-1H-indol-4-yl]oxy] acetate, a compound represented by the formula:

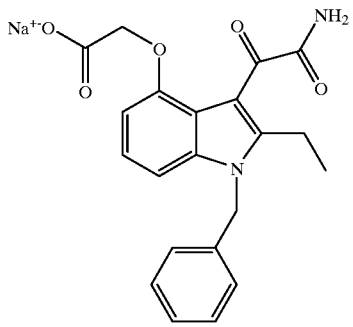

The term, "mammal", includes a human as well as related important veterinary species of mammals, domesticated quadrupeds such as monkeys, dogs, cats, horses, sheep, pigs, goats, and cows.

The term, "Inflammatory Diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes," polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases included or maintained by sPLA$_2$ mediated release of fatty acid and the arachidonic acid cascade and its deleterious products.

The term, "collapse temperature," describes the glass transition temperature for amorphous solids or eutectic temperature for crystalline solids. Collapse temperature is that temperature above which the product is not completely frozen. Freeze dry microscoscropy enables measurement of the temperature at which frozen solutions begin to lose their rigid structure during a sublimation process. For sodium [[3-(2-amino-1,2-dioxoethyl)-2-ethyl-1-(phenylmethyl)-1H-indol-4-yl]oxy]acetate frozen solutions, the collapse temperature before annealing has been measured at about −33° C. while the collapse temperature after annealing is about −13° C.

The term, "Solubilizer", refers to a chelating agent. An "effective amount of Solubilizer" is a quantity of Solubilizer that permits the Active Ingredient to form stable aqueous solutions suitable for medical use.

The term, "Stabilizer", refers to a solid sugar or sugar-alcohol. An "effective amount of Stabilizer" is a quantity of Stabilizer that permits the lyophilized composition to be readily dissolved to form aqueous solutions suitable for medical use.

The term, "dose-concentrate" refers to a solution of pharmaceutical formulation. The dose-concentrate may be held in the container where it was formed by adding aqueous solvent to pharmaceutical formulation or it may be removed and held externally. The dose-concentrate may be used as is, but is generally further diluted to a unit dosage concentration for administration to a mammal. The entire volume of the dose-concentrate or aliquots thereof may be used in preparing unit dose(s) for treatment by the method of this invention.

The term, "the equivalent acid of Active Ingredient" or "the equivalent acid of Compound (I)" means [[3-(2-Amino-1,2-dioxoethyl)-2-ethyl-1-(phenylmethyl)-1H-indol-4-yl]oxy]acetic acid. In this specification, weight of Active Ingredient is shown by the actual weight of sodium [[3-(2-amino-1,2-dioxoethyl)-2-ethyl-1-(phenylmethyl)-1H-indol-4-yl]oxy]acetate. In showing proportion (weight %) of Active ingredient, however, it is calculated based on the equivalent acid of Active Ingredient. Thus weights of Active Ingredient must be multiplied by the factor 100/105.8 to calculate the equivalent weight of the equivalent acid.

Methods of Making the Active Ingredient:

Compound (I) to be used in the present invention can be synthesized by the known process described in JP-A 7 285933 and can be used for the compositions and preparations of the present invention in any state, including crystal, amorphous, hydrate, solvate, or a mixture of such forms. Similarly, Compound (I) may be prepared by the synthesis schemes taught in U.S. Pat. No. 5,654,326; the disclosure of which is incorporated herein by reference. Another method of making Compound (I) is described in U.S. patent application Ser. No. 09/105381, filed Jun. 26, 1998 and titled, "Process for Preparing 4-substituted 1-H-Indole-3-glyoxyamides" the entire disclosure of which is incorporated herein by reference.

An illustrative synthesis of Compound (I) is as follows in Steps (A) through (F):

Preparation of Sodium [[3-(2-Amino-1,2-dioxoethyl)-2-ethyl-1-(phenylmethyl)-1H-indol-4-yl]oxy]acetate, a compound represented by the formula:

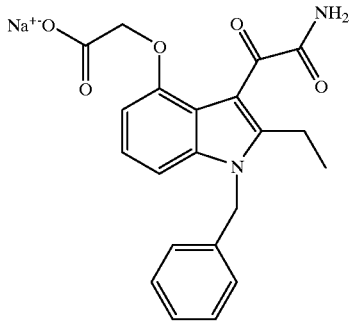

Step A. Preparation of 2-Ethyl-4-methoxy-1H-indole:

A solution of 140 mL (0.18 mol) of 1.3M sec-butyl lithium in cyclohexane was added slowly to N-tert-butoxycarbonyl-3-methoxy-2-methylaniline (21.3 g, 0.09 mol) in 250 mL of THF keeping the temperature below −40° C. with a dry ice-ethanol bath. The bath was removed and the temperature allowed to rise to 0° C. and then the bath replaced. After the temperature had cooled to −60° C., 18.5 g (0.18 mol) of N-methoxy-N-methylpropanamide in an equal volume of THF was added dropwise. The reaction mixture was stirred 5 minutes, the cooling bath removed and stirred an additional 18 hours. It was then poured into a mixture of 300 mL of ether and 400 mL of 0.5N HCl. The organic layer was separated, washed with water, brine, dried over MgSO$_4$, and concentrated at reduced pressure to give 25.5 g of a crude of 1-[2-(tert-butoxycarbonylamino)-6-methoxyphenyl]-2-butanone. This material was dissolved in 250 mL of methylene chloride and 50 mL of trifluoroacetic acid and stirred for a total of 17 hours. The mixture was concentrated at reduced pressure and ethyl acetate and water added to the remaining oil. The ethyl acetate was separated, washed with brine, dried (MgSO$_4$) and concentrated. The residue was chromatographed three times on silica eluting with 20% EtOAc/hexane to give 13.9 g of 2-ethyl-4-methoxy-1H-indole.

Step B. Preparation of 2-Ethyl-4-methoxy-1-(phenylmethyl)-1H-indole:

2-Ethyl-4-methoxy-1H-indole (4.2 g, 24 mmol) was dissolved in 30 mL of DMF and 960 mg (24 mmol) of 60% NaH/minerial oil was added. After 1.5 hours, 2.9 mL(24 mmol) of benzyl bromide was added. After 4 hours, the mixture was diluted with water and extracted twice with ethyl acetate. The combined ethyl acetate was washed with brine, dried (MgSO$_4$) and concentrated at reduced pressure. The residue was chromatographed on silica gel and eluted with 20% EtOAc/hexane to give 3.1 g (49% yield) of 2-ethyl-4-methoxy-1-(phenylmethyl)-1H-indole.

Step C. Preparation of 2-Ethyl-4-hydroxy-1-(phenylmethyl)-1H-indole:

3.1 g (11.7 mmol) of 2-ethyl-4-methoxy-1-(phenylmethyl)-1H-indole was O-demethylated by treating it with 48.6 mL of 1M BBr$_3$ in methylene chloride with stirring at room temperature for 5 hours, followed by concentration at reduced pressure. The residue was dissolved in ethyl acetate, washed with brine and dried (MgSO$_4$). After concentrating at reduced pressure, the residue was chromatographed on silica gel eluting with 20% EtOAc/hexane to give 1.58 g (54% yield) of 2-ethyl-4-hydroxy-1-(phenylmethyl)-1H-indole.

Step D: Preparation of [[2-Ethyl-1-(phenylmethyl)-1H-indol-4-yl]oxy]acetic acid methyl ester.

2-ethyl-4-hydroxy-1-(phenylmethyl)-1H-indole (1.56 g, 6.2 mmol) was added to a mixture of 248 mg (6.2 mmol) of 60% NaH/mineral oil in 20 mL DMF and stirred for 0.67 hour.

Then 0.6 mL(6.2 mmol) of methyl bromoacetate was added and stirring was continued for 17 hours. The mixture was diluted with water and extracted with ethyl acetate. The ethyl acetate solution was washed with brine, dried (MgSO$_4$), and concentrated at reduced pressure. The residue was chromatographed on silica gel eluting with 20% EtOAc/hexane, to give 1.37 g (69% yield) of [[2-ethyl-1-(phenylmethyl)-1H-indol-4-yl]oxy]acetic acid methyl ester.

Step E. Preparation of [[3-(2-Amino-1,2-dioxoethyl)-2-ethyl-1-(phenylmethyl)-1H-indol-4-yl]oxy]acetic acid methyl ester:

Oxalyl chloride (0.4 mL, 4.2 mmol) was added to 1.36 g (4.2 mmol) of [[2-ethyl-1-(phenylmethyl)-1H-indol-4-yl]oxy]acetic acid methyl ester in 10 mL of methylene chloride and the mixture stirred for 1.5 hours. The mixture was concentrated at reduced pressure and residue taken up in 10 mL of methylene chloride. Anhydrous ammonia was bubbled in for 0.25 hours, the mixture stirred for 1.5 hours and evaporated at reduced pressure. The residue was stirred with 20 mL of ethyl acetate and the mixture filtered. The filtrate was concentrated to give 1.37 g of a mixture of [[3-(2-amino-1,2-dioxoethyl)-2-ethyl-1-(phenylmethyl)-1H-indol-4-yl]oxy]acetic acid methyl ester and ammonium chloride. This mixture melted at 172–187° C.

Step F. Preparation of [[3-(2-Amino-1,2-dioxoethyl)-2-ethyl-1-(phenylmethyl)-1H-indol-4-yl]oxy]acetic acid, sodium salt:

A mixture of 788 mg (2 mmol) of [3-(2-amino-1,2-dioxoethyl)-2-ethyl-1-(phenylmethyl)-1H-indol-4-yl]oxy] acetic acid methyl ester, 10 mL of 1 n NaOH and 30 mL of MeOH is heated to maintain reflux for 0.5 hour, stirred at room temperature for 0.5 hour and concentrated at reduced pressure.

Identity and Proportion of Ingredients in the Pharmaceutical Compositions and Lyophilized Compositions of the Invention:

In one embodiment, the present invention is a pharmaceutical composition which comprises Compound (I) as Active Ingredient and an effective amount of a Solubilizer acting as a chelating agent, for example, preferably at least one compound selected from citric acid, edetic acid (e.g., disodium EDTA), polyphosphoric acid and their salts, more preferably sodium citrate. Examples of polyphosphoric acid and their salts are potassium polyphosphate as described in the Japanese standards of food additives, 6th ed., and sodium polyphosphate as described in the Japanese standards of food additives, 6th ed., or the Japanese standards of cosmetic ingredients, 2nd ed. Sodium citrate is available as trisodium citrate anhydrous, trisodium citrate dihydrate, and trisodium citrate pentahydrate, but is most conveniently and preferably used in the form of trisodium citrate dyhydrate (mol. wt. 294.10).

The amount of the Solubilizer varies with the kind of the Solubilizer and the concentration of Compound (I), and may be from about 1% to about 400% (w/w), preferably 1 to 200% (w/w), most preferably 1 to 100% (w/w) of the amount of the equivalent acid of Compound (I). For pharmaceutical compositions using sodium citrate the weight of Solubilizer is from 10% to 150% (w/w) and more preferably 25% to 100% (w/w) of the amount of the equivalent acid of Compound (I).

Preferably, the pharmaceutical composition described in the preceding paragraph also has an effective amount of a Stabilizer. The Stabilizer is at least one pharmaceutically acceptable compound selected from solid sugars and sugar-alcohols, more preferably at least one compound selected from mannitol, xylitol, sorbitol, glucose, fructose, lactose and maltose. Mannitol is the most preferred Stabilizer ingredient.

The amount of the Stabilizer varies with the kind of Stabilizer and the concentration of Compound (I), and may be 40% to 500% (w/w), preferably from 50% to 300% (w/w), more preferably from 50 to 250% (w/w), most preferably from 50% to 200% (w/w) of the amount of the equivalent acid of Compound (I).

Without departing from the object and scope of the present invention, other pharmaceutically acceptable additive agents may optionally be added to the preparations of the present invention. Where a solution according to the invention is prepared for injection, an isotonizing agent, a soothing agent or other additives may be added thereto.

Preferably, the pharmaceutical compositions described above are salt-free except for the Active Ingredient, the Solubilizer and the Stabilizer.

Lyophilized Compositions of the Invention:

Preferably, the pharmaceutical compositions described in the preceding section are lyophilized. Most preferably the lyophilized composition is prepared with an annealing step by employing the collapse temperature characteristics of Compound (I).

The lyophilized composition contains Solubilizer from about 1 to about 200% (w/w) of the amount of the equivalent acid of Compound (I). The proportions of the Solubilizer are the same as those set out in the preceding section for the pharmaceutical composition. When the Solubilizer is disodium EDTA (or its acid or other salts) it is preferably used from about 1% to about 15% (w/w) of the amount of the equivalent acid of Compound (I). When the Solubilizer is trisodium citrate dihydrate it is preferably used from about 10% to about 100% of the amount of Active Ingredient.

The identity and proportions of Stabilizer are the same as those set out in the preceding section for the pharmaceutical composition. Mannitol is most preferred as the Stabilizer ingredient of the lyophilized compositions of the invention. Table 1 lists Specific Preferred Lypholyzed Compositions of the Invention (all amounts in milligrams):

TABLE 1

| A.I.  | Na Citrate | Mannitol | EDTA |
|-------|------------|----------|------|
| 105.8 | 50         | 200      | —    |
| 105.8 | 100        | 200      | —    |
| 105.8 | 75         | 200      | —    |
| 105.8 | —          | 200      | 1    |
| 105.8 | —          | 200      | 8    |
| 105.8 | —          | 200      | 15   |

A.I. = Active Ingredient,
Na Citrate = trisodium citrate dihydrate
EDTA = ethylenediaminetetraacetic acid, disodium salt Preferably, the solid lyophilized compositions of the invention are substantially salt-free, except for Compound (I) and the Stabilizer and Solubilizer contained therein.

The lyophilized pharmaceutical formulation can be dissolved in a pharmaceutically acceptable carrier, such as sterile water, sterile water optionally containing saline and/ or sterile water containing sugars. For example, for intravenous injection the compositions of the invention may be dissolved in at a concentration of 2 mg/ml in a 4% dextrose/ 0.5% Na citrate aqueous solution.

As used herein, the terms "lyophilized compositions", "pharmaceutical compositions" and "pharmaceutical preparations" refer to all preparations described in "General rules for preparation" in the Japanese Pharmacopoeia, preferably those that are solutions and injection preparations, more preferably solutions for injection and lyophilized preparations for injection.

Method of Making the Lyophilized Compositions of the Invention:

The lyophilized compositions of the present invention refer to a preparation prepared by freeze drying a solution containing Compound (I), optionally being subjected to a heat treating process, and being dried in a high vacuum for sublimating water. Such lyophilized preparations include lyophilized preparations for injection as mentioned above. The lyophilized preparation may be produced by conventional methods including tray lyophilization, spray lyophilization and vial lyophilization methods. Vial lyophilization is advantageous for preparing multi-dosage units of the invention as described, infra.

In order to obtain a solution of Compound (I) by the process of the present invention, Compound (I), a Solubilizer and a solvent are mixed and stirred until the mixture becomes clear. The solvent is preferably an aqueous solvent such as water, purified water, water for injection, isotonic sodium chloride solution or glucose injection as described in the Japanese Pharmacopoeia, more preferably a salt-free aqueous solvent such as water, purified water, water for injection or glucose solutions for injection.

Alternatively, a suitable solvent for forming a solution from the composition of the invention is any injectable solution as further exemplified by those described in The United States Pharmacopeia (1995, ISBN 0195-7996), for example, "Sterile Water for Injection", "Dextrose and Sodium Chloride Injection", "Dextrose Injection", "Mannitol Injection" or "Mannitol in Sodium Chloride Injection."

In order to obtain a lyophilized preparation of Compound (I) by the process of the present invention, first, a processing solution prior to lyophilization is prepared. The processing solution before lyophilization is a solution prepared by mixing and stirring Compound (I), a Solubilizer and a solvent, preferably Compound (I), a Solubilizer, a Stabilizer and a solvent, until the mixture becomes clear. For the sequence of addition of the ingredients to the solvent it is highly preferred to first dissolve the Solubilizer and Stabilizer, and thereafter dissolve Compound (I). The solvent is preferably an aqueous solvent such as previously set out above and as described in the Japanese Pharmacopoeia, and more preferably a salt-free aqueous solvent such as water, water for injection or glucose injection. The processing solution before lyophilization of Compound (I) may contain Compound (I) at a concentration of from about 0.5% to 2% (w/w).

If desired, the processing solution before lyophilization may be subjected to a filtration process. The filtration process includes, for example in the case of injection preparations, a sterilizing filtration and/or an ultra filtration of the processing solution before lyophilization to eliminate microorganisms or other contaminating matter from the processing solution before lyophilization.

If desired, the processing solution before lyophilization may be subjected to a distributing process. The distributing process includes, for example in the case of vial lyophilizations, a process distributing a suitable volume of the processing solution before lyophilization into vials taking the concentration of Compound (I) into consideration in order that vial products carry a desired amount of Compound (I).

A lyophilization process is performed as follows:

Preferably, the lyophilized composition is prepared by a sequential heating and cooling process. A process for preparing a lyophilized composition comprises the sequential steps of:

(a) dissolving lyophilized composition ingredients comprising Sodium [[3-(2-amino-1,2-dioxoethyl)-2-ethyl-1-phenylmethyl)-1H-indol-4-yl]oxy]acetate, Soulubilizer, and Stabilizer in an aqueous solvent;

(b) cooling the processing solution of step (a) to a temperature below −33° C.;

(c) heating the product of step (b) to a temperature above −33° C.;

(d) cooling the product of step (c) to a temperature below −33° C.;

(e) heating the product of step (d) to a temperature above −13° C., under subatmospheric pressure for a time sufficient to remove water from the aqueous solvent and yield a solid lyophilized product.

Preferably, step (a) is conducted by dissolving in an aqueous solvent: Sodium [[3-(2-amino-1,2-dioxoethyl)-2-ethyl-1-phenylmethyl)-1H-indol-4-yl]oxy]acetate; Solubilizer selected from citric acid, edetic acid, polyphosphoric acid and their salts, the amount of which is 1 to 100% (w/w)

of the amount of the equivalent acid of Compound (I); and Stabilizer selected from mannitol, xylitol, sorbitol, glucose, fructose, lactose and maltose, the amount of which is 50 to 200% (w/w) of the equivalent acid of Compound (I). Moreover, each of steps (b), (c), (d) and (e) is preferably conducted for a period of at least one-half hour, and step (e) is performed at a subatmospheric pressure less than about 133 Pa (1000 milliTorr).

Preferred parameters in the lyophilization process are those wherein Compound (I) is frozen by cooling to −35° C. to −45° C. This cooling step is performed preferably over 2 to 4 hours. This process is herein after referred to as the "primary freezing process".

If desired, the frozen solution obtained in the primary freezing process is then warmed to −5° C. to −25° C. preferably from −10° C. to −20° C. This warming step is performed over 3 hours, preferably from 5 to 10 hours. This process is herein after referred to as the "heat treating process".

The composition obtained in the heat treating process is re-frozen, preferably from −35° C. to −45° C. This cooling step is performed preferably over 2 to 4 hours. This process is herein after referred to as the "re-freezing process".

The composition obtained through the primary freezing process, the heat treating process and the re-freezing process, is dried under a high vacuum by sublimating water according to methods known to those skilled in the art. Thus, a lyophilized preparation of the present invention is obtained. If desired, two step drying in which the temperature and the degree of vacuum are different may be performed for completely removing water. This process is herein after referred to as the "drying process". If the two step drying is performed, these process are referred to as the "primary drying" process and the "secondary drying" process.

The lyophilization process removes most of the water originally present, but the final product lyophilized composition may contain some free water. Typically, the water content can range from 0.5% to 5.0% weight percent. More typically, the water content ranges from 0.8% to 2.0%.

Dose-concentrate and Unit Dosage Configurations of the Invention:

A dose-concentrate configuration of the formulation of the invention is a sealed container holding an amount of lyophilized pharmaceutical formulation of the invention employed over a standard treatment interval such as 12 or 24 hours. The dose-concentrate configuration is prepared by placing lyophilized composition in a container (e.g., glass or plastic bottles, vials, ampoules) in sufficient amount to treat a mammal for a period ranging from 1 hour to 1 week, but preferably from 4 hours to 48 hours. The container preferably also contains an empty space of sufficient size to permit (i) addition of aqueous solvent plus (ii) additional space as necessary to permit agitation and effect complete solution of the lyophilized composition in the added aqueous solvent. The container may be equipped with a penetrable top, for example, a rubber seal, so that aqueous solvent may be added by penetrating the seal with a hypodermic syringe and the concentrate subsequently removed by the same means.

An example of a dose-concentrate configuration is a glass vial having a capacity of from about 10 to about 100 milliliters containing 50 to 5000 milligrams of lyophilized pharmaceutical composition. A specific example, is a 20 glass bottle with a rubber seal having lyophilized pharmaceutical composition containing 105.8 mg of Compound (I), 50 mg of trisodium citrate dihydrate, and 200 mg of mannitol. The empty space above the solid composition has ample room for addition of a solvent such as sterile water for injection plus room to agitate the total contents.

The addition of the aqueous solvent to the dose-concentrate configuration results in a liquid concentrate which may then be conveniently used to form unit dosages of liquid pharmaceutical formulations by removing aliquot portions or entire contents for dilution as set out in the following section.

Unit Dose of the Invention:

The concentrated solution of lyophilized composition formed in the dose-concentrate container (typically of a bright yellow color) is added to an IV (intravenous) container containing a suitable aqueous solvent. Useful solvents are standard solutions for injection as previously described (e.g., 5% dextrose or sterile water for injection, etc.). Typical unit dosage IV bags are conventional glass or plastic containers having inlet and outlet means and having standard (e.g., 250 ml and 500 ml) capacities. The concentrated solution of lyophilized pharmaceutical formulation is added to the unit dose IV bag in an amount to achieve a concentration of about 0.05 to 2.0 mg of Compound (I) per ml and preferably from 0.2 to 0.8 mg per ml.

Without departing from the object and scope of the present invention, other pharmaceutically acceptable additive agents may be added to the lyophilized preparations of the present invention. Where the lyophilized preparation is to be used for injection, an isotonizing agent or a soothing agent or other additives may be added thereto.

Use of the Composition of the Invention for Treatment of Inflammatory Diseases:

The improved method of treatment using the lyophilized composition may be practiced as follows:

The diluted formulations of this invention are given by injection, either subcutaneously or into muscle tissue or by injection into a vein. Intravenous injection is the preferred mode of delivery to the mammal being treated and offers the advantage of a quick effect and rapid access into the circulation system, particularly in emergency situations.

Preferably the lyophilized pharmaceutical formulation of this invention is diluted with aqueous solvent suitable for injection and a liquid unit dosage form prepared (viz., IV Bag) for administration to a mammal. An IV bag for pediatric use may have a 100 ml capacity.

It may be appreciated that it may be necessary to make routine variations to the dosage depending on the age and condition of the patient. The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic Compound (I) dosage level of from about 0.01 mg/kg to about 50 mg/kg of body weight of an Active ingredient of this invention.

This invention is a method of treating or preventing sepsis by administering to a mammal in need thereof a therapeutically effective amount of a solution prepared by dissolving the pharmaceutical formulation of this invention. The administration to a septic patient may be either continuous or intermittent.

The decision to begin the therapy for sepsis will be based upon the appearance of the clinical manifestations of sepsis or laboratory tests which show initiation of the sepsis cascade (inclusive of renal complications or coagulation abnormalities or multiple organ failure). Typical clinical manifestations are fever, chills, tachycardia, tachypnea, altered mental state, hypothermia, hyperthermia, accelerated or repressed breathing or heart rates, increased or decreased white blood cell count, and hypotension. These and other symptoms are well known in the art as set out in standard references such as, Harrison's Principles of Internal Medicine (ISBN 0-07-032370-4) 1994, pages 511–515.

The decision to determine the length of therapy may be supported by standard clinical laboratory results from commercially available assays or instrumentation supporting the eradication of the symptoms defining sepsis. The method of the invention may be practiced by continuously or intermittently administering a therapeutically effective dose of the solution prepared from the lyophilized pharmaceutical formulation for as long as deemed efficacious for the treatment of the septic episode. The administration can be conducted for up to a total of about 60 days with a preferred course of therapy lasting for up to 10 days.

The decision to end therapy by the method of the invention may be supported by standard clinical laboratory results from commercially available assays or instrumentation or the disappearance of clinical symptoms characteristic of sepsis. The therapy may be restarted upon the return of sepsis.

Pediatric forms of sepsis are also successfully treated by the methods and compositions of this invention.

EXAMPLES

The present invention is more specifically described and explained by, but in no way limited to, the following Examples:

Example 1 and Comparative Example 1

Solutions were prepared by mixing the materials of Table 2 with a solvent, the solvent being one of water for injection, isotonic sodium chloride solution and 5% glucose solution at a volume of 20 ml.

TABLE 2

Preparation of solutions

|  | Comparative Example 1-1 | Example 1-1 | Example 1-2 | Example 1-3 | Example 1-4 | Example 1-5 |
|---|---|---|---|---|---|---|
| A.I. | 20 mg | 20 mg | 20 mg | 20 mg | 20 mg | 20 mg |
| Na Citrate |  | 4 mg | 8 mg | 12 mg | 16 mg | 20 mg |

Tests for solubility were performed by inspecting the solutions immediately after being prepared and after 24 hours of storage at room temperature with the unaided eyes. Tables 3 to 5 show the results of the test for solubility. Each table shows clearly that addition of the Solubilizer of the present invention improves stability of the solution.

TABLE 3

Result of solubility tests (added 20 ml of water 1 to the preparation of Table 1)

|  | Comparative example 1-1-20W | Example 1-1-20W | Example 1-2-20W | Example 1-3-20W | Example 1-4-20W | Example 1-5-20W |
|---|---|---|---|---|---|---|
| Initial | O-Δ | 0 | 0 | 0 | 0 | 0 |
| Storage for 24 hours | Δ | 0-Δ | 0 | 0 | 0 | 0 |

TABLE 4

Result of solubility tests (added 20 ml of saline 2 to the preparation of Table 1)

|  | Comparative example 1-1-20S | Example 1-1-20S | Example 1-2-20S | Example 1-3-20S | Example 1-4-20S | Example 1-5-20S |
|---|---|---|---|---|---|---|
| Initial | O-Δ | 0 | 0 | 0 | 0 | 0 |
| Storage for 24 hours | Δ | 0 | 0 | 0 | 0 | 0 |

TABLE 5

Result of solubility tests (added 20 ml of glucose soln. 3 to the preparation of Table 1)

|  | Comparative Example 1-1-20G | Example 1-1-20G | Example 1-2-20G | Example 1-3-20G | Example 1-4-20G | Example 1-5-20G |
|---|---|---|---|---|---|---|
| Initial | Δ | 0 | 0 | 0 | 0 | 0 |
| Storage for 24 hours | Δ | 0 | 0 | 0 | 0 | 0 |

Explanation of symbols in Tables 2 to 4
0 . . . Excellent solution
Δ Crystals appeared slightly in solution
1 water . . . water for injection
2 saline . . . isotonic sodium chloride solution
3 glucose soln. - 5% glucose solution Examples 2–4 & Comparative Example 2

The processing solution before lyophilization was prepared by dissolving the materials of Table 6 in water for injection as a solvent as described in the Japanese Pharmacopoeia such that the concentration of Compound (I) was 10 mg/g. The processing solution before lyophilization was subjected to a sterilizing filtration using a membrane filter of which the pore size was 0.22 micrometer and then distributed in glass vials.

The lyophilization was performed as follows. The primary freezing process was done for 3 hours at −40° C., the heat treating process for 10 hours at −10° C., and the re-freezing process for 3 hours was at −40° C. Then, the primary drying process was performed for 24 hours at 0° C., 2.0 Pa and the secondary drying process for 5 hours at 60° C., 2.0 Pa. Thus, lyophilized preparations of Examples 2 to 4 were obtained. For comparison, the preparation of Comparative example 2 was produced by the method in which the filtration process and the distribution process was the same as those of Examples 2–4 and the lyophilization was substantially the same as the process of Examples 2–4, that is the primary freezing process was done for 3 hours at −40° C., the primary drying step for 20 hours at 10° C., 10 Pa, and the secondary drying step for 5 hours at 40° C., 2.0 Pa.

TABLE 6

Composition of lyophilized preparations (in 1 vial)

|  | Example 2 | Example 3 | Example 4 | Comparative example 2 |
|---|---|---|---|---|
| A.I. | 53 mg | 53 mg | 53 mg | 100 mg |
| Na Citrate | 20 mg | 20 mg | 20 mg |  |
| Mannitol | — | 25 mg | 50 mg |  |

A.I. = Active Ingredient,
Na Citrate = trisodium citrate dihydrate

Table 7 shows the appearance of the lyophilization cakes immediately after lyophilization in Examples 2 to 4. Addition of the Stabilizer of the present invention gave excellent lyophilized preparations in which the lyophilized cake does not have cracked parts, shrunken parts and a thin layer on the surface of the cake and in which the cake was not colored much.

TABLE 7

Appearance of cake after lyophilization

|  | Example 2 | Example 3 | Example 4 | Comparative Example 2 |
|---|---|---|---|---|
| Cake on the Upside of Vial | None | None | None | Some |
| Color | Yellow | Light yellow | Dark white | Dark yellow |
| Appearance of cake | Shrunken Parts on The surface Of cake | Shrunken parts on the surface of cake | Excellent Cake[1] | Cracked and Shrunken Cake |

[1]This cake does not have cracked parts, shrunken parts and a thin layer on the surface of cake.

A content uniformity test on Compound (I) of 10 vials of the lyophilized preparation obtained in Example 4 was performed. The content of Compound (I) was measured by the HPLC method. The content of Compound (I) in one vial was 99.0% to 103.4% relative to the theoretical value of the amount of Compound (I), which indicates the lyophilized preparation of the present invention has satisfactory uniformity of content.

The reconstitution times of 10 vials of the lyophilized preparation obtained in Example 4 were measured. The measurement of reconstitution time was performed by adding the sample to 10 ml of water for injection, shaking the resulting mixture at 200 times/min., and measuring the period of time until the samples were completely dissolved. The time of reconstitution was from 7 to 18 seconds. The lyophilized preparation of the present invention has a satisfactory reconstitution property.

Three hermetic vials of the lyophilized preparation of Example 2 were tested with respect to storage stability at 60° C. for 2 months. The residual percentages of content in 3 vials were all 99% relative to initial value immediately after lyophilization. The lyophilized preparation of the present invention has satisfactory storage stability.

Example 5

The processing solution before lyophilization was prepared by dissolving the materials of Table 8 in water for injection as a solvent as described in the Japanese Pharmacopoeia such that the concentration of Compound (I) was 15 mg/g. The processing solution before lyophilization was subjected to a sterilizing filtration using a membrane filter of which the pore size was 0.22 micrometer and then distributed in glass vials.

TABLE 8

Composition of lyophilized preparations (in 1 vial)

|  | Example 5 |
|---|---|
| A.I. | 127 mg |
| Na Citrate | 36 mg |
| Mannitol | 180 mg |

A.I. = Active Ingredient,
Na Citrate = trisodium citrate dihydrate

The lyophilization was performed as follows. The primary freezing step was done for 3 hours at −40° C., the heat treating step for 10 hours at −10° C., and the re-freezing step for 3 hours at −40° C. Then, the primary drying step was performed for 60 hours at 0° C., 10 Pa and the secondary drying step for 5 hours at 60° C., 4 Pa. Thus the lyophilized preparation of Example 5 was obtained.

The appearance of cake immediately after lyophilization in Example 5 was observed. The lyophilized cake did not have cracked parts, shrunk parts and a thin layer on the surface of cake and the color of the cake was dark white.

The content uniformity test on Compound (I) of 10 vials of the lyophilized preparation obtained in Example 5 was performed. The content of Compound (I) was measured by the HPLC method. The content of Compound (I) per vial was 99.8 to 101.3% relative to the theoretical value of the amount of Compound (I), which indicates the lyophilized preparation of the present invention has satisfactory uniformity of content.

The reconstitution time of 10 vials of the lyophilized preparation obtained in Example 5 was measured. The measurement of reconstitution time was performed by adding 10 ml of water for injection to each of the vials, shaking the resulting mixture at 200 times/min., and measuring the period of time until the cake was completely dissolved. The time of reconstitution was from 22 to 29 seconds. The lyophilized preparation of the present invention has a satisfactory reconstitution property.

Example 6

Another example of preparing the lyophilized composition of the invention is as follows:
Preparation of a Solution Suitable for Lyophilization (processing solution):

(A) A volume of water equal to approximately 80% of the final volume of solid lyophilized pharmaceutical composition was placed in the manufacturing vessel.

(B) Mannitol and sodium citrate were first added to the vessel and stirred until complete dissolution took place.

(C) Sodium [[3-(2-amino-1,2-dioxoethyl)-2-ethyl-1-(phenylmethyl)-1H-indol-4-yl]oxy]acetate was added to the vessel and stirred until completely dissolved.

(D) The remaining water was added to achieve a final Active Ingredient concentration of 10 mg per ml.

The sequential process of lyophilization was performed as follows:

1. Sealable vials containing 10 ml of the processing solution prepared in the preceding step of this example were placed on the shelves of a freeze dryer pre-cooled to 0° C.

2. After all the vials had been loaded onto the shelves, the shelf temperature was cooled to −40° C. Once product temperature of the monitored vials is −40° C., the vials were held at this temperature for 2 hours.

3. The shelf temperature was then raised to −10° C. to anneal the frozen solution. This temperature was above the collapse temperature of the solution which permitted the crystallization of the solutes. The product was held at this temperature for several hours.

4. Shelf temperature was then decreased to −40° C. again for a short period of time to complete the annealing (temperature cycling) process.

5. Primary drying was then initiated by increasing shelf temperature to 0° C. and decreasing chamber pressure to approximately 13.3 Pa (100 milliTorr). Primary drying lasted for more than 24 hours until product temperature begins to rise, signaling that solvent water has been removed.

6. Secondary drying was achieved by raising the chamber temperature to 28° C. with chamber pressure remaining at 13.3 Pa.(100 milliTorr) and lasting for several hours. The product was a solid uncracked cake of a off-white color.

As the above Examples show, the present invention provides pharmaceutical compositions of Compound (I) which are stable and have good reconstitution properties.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

What is claimed is:

1. A pharmaceutical composition which comprises sodium [[3-(2-amino-1,2-dioxoethyl)-2-ethyl-1-phenylmethyl)-1H-indol-4-yl]oxy]acetate as Active Ingredient; a chelating agent as a Solubilizer; and at least one compound selected from the group consisting of solid sugars and sugar-alcohols, as a Stabilizer.

2. A pharmaceutical composition as claimed in claim 1 wherein the chelating agent is at least one compound selected from the group consisting of citric acid, edetic acid, polyphosphoric acid and their salts.

3. A pharmaceutical composition as claimed in claim 1 wherein the chelating agent is sodium citrate.

4. A pharmaceutical composition as claimed in claim 1 wherein the amount of the chelating agent is from 1% to 400% (w/w) of the amount of the equivalent acid of Active Ingredient.

5. A pharmaceutical composition as claimed in claim 3 wherein the amount of sodium citrate is from 10% to 100% (w/w) of the amount of the equivalent acid of Active Ingredient.

6. A pharmaceutical composition as claimed in claim 1 which is salt-free except for the Active Ingredient and the chelating agent.

7. A pharmaceutical composition as claimed in claim 1 which is lyophilized.

8. A pharmaceutical composition as claimed in claim 1 wherein the Stabilizer is at least one compound selected from the group consisting of mannitol, xylitol, sorbitol, glucose, fructose, lactose and maltose.

9. A pharmaceutical composition as claimed in claim 1 wherein the Stabilizer is mannitol.

10. A pharmaceutical composition as claimed in claim 1 wherein the amount of the Stabilizer is from 40% to 500% (w/w) of the amount of the equivalent acid of Active Ingredient.

11. A lyophilized composition which comprises sodium [[3-(2-amino-1,2-dioxoethyl)-2-ethyl-1-phenylmethyl)-1H-indol-4-yl]oxy]acetate as Active Ingredient; a Solubilizer chelating agent selected from the group consisting of citric acid, edetic acid, polyphosphoric acid and its salts; and a Stabilizer selected from the group consisting of mannitol, xylitol, sorbitol, glucose, fructose, lactose and maltose.

12. The composition of claim 11 wherein per the amount of the equivalent acid of Active Ingredient, the Stabilizer is present at 1 to 100% (w/w) and the Solubilizer is present at 50 to 200% (w/w).

13. The composition of any one of claims 1 or 11 which is salt-free, except for Active Ingredient, Solubilizer and Stabilizer.

14. A method of inhibiting $sPLA_2$ mediated release of fatty acid which comprises contacting $sPLA_2$ with a therapeutically effective amount of a solution prepared from the composition of claim 1 or 11.

15. A method of treating a mammal to alleviate the pathological effects of Inflammatory Diseases; wherein the method comprises parenterally administering to said mammal a therapeutically effective amount of a solution prepared from the formulation of claim 1 or 11.

16. A dose-concentrate containing sealed container containing lyophilized composition of claim 1 or 11, said container having a space sufficient for introduction of a volume of aqueous solvent sufficient to form a concentrated solution of said formulation.

17. A unit dose IV bag or IV bottle containing a liquid for intravenous injection in the treatment of Inflammatory Diseases, said liquid comprising an aqueous solution prepared from the composition of claim 1 or 11.

18. A method of making a pharmaceutical formulation, comprising the steps of:

a) dissolving a composition comprising Sodium [[3-(2-amino-1,2-dioxoethyl)-2-ethyl-1-phenylmethyl)-1H-indol-4-yl]oxy]acetate, Solubilizer, and Stabilizer in an aqueous solvent;

b) cooling the processing solution of step (a) to a temperature below about −33° C.;

c) heating the product of step (b) to a temperature above about −33° C.;

d) cooling the product of step (c) to a temperature below about −33° C.;

e) heating the product of step (d) to a temperature above −13° C., under subatmospheric pressure for a time sufficient to remove water from the aqueous solvent and yield a solid lyophilized product.

19. The process of claim 18 wherein:

Steps (b), (c), (d) and (e) are each conducted for a period of at least one-half hour and step (e) is performed at a subatmospheric pressure less than 133 Pa.

20. A lyophilized composition prepared by the process of claim 18.

21. A lyophilized composition which comprises sodium [[3-(2-amino-1,2-dioxoethyl)-2-ethyl-1-phenylmethyl)-1H-indol-4-yl]oxy]acetate as Active Ingredient, and a Solubilizer selected from at least one compound which is selected from the group consisting of citric acid, edetic acid, polyphosphoric acid and their salts; and a Stabilizer selected from at least one compound which is selected from the group consisting of mannitol, xylitol, sorbitol, glucose, fructose, lactose and maltose.

22. A lyophilized composition which comprises sodium [[3-(2-amino-1,2-dioxoethyl)-2-ethyl-1-phenylmethyl)-1H-indol-4-yl]oxy]acetate as Active Ingredient; a Solubilizer which is sodium citrate dihydrate or disodium EDTA; and a Stabilizer which is mannitol.

23. A method of making a pharmaceutical formulation, comprising the steps of:
   a) dissolving a composition comprising Sodium [[3-(2-amino-1,2-dioxoethyl)-2-ethyl-1-phenylmethyl)-1H-indol-4-yl]oxy]actate, Solubilizer, and Stabilizer in an aqueous solvent;
   b) cooling the processing solution of step (a) to a temperature below about −33° C.;
   c) heating the product of step (b) to a temperature above about −33° C.;
   d) cooling the product of step (c) to a temperature below about −33° C.;
   e) heating the product of step (d) to a temperature above −13° C., under subatmospheric pressure for a time sufficient to remove water from the aqueous solvent and yield a solid lyophilized product,
   wherein Step (a) is conducted by dissolving in an aqueous solvent: Sodium [[3-(2-amino-1,2-dioxoethyl)-2-ethyl-1-phenylmethyl)-1H-indol-4-yl]oxy]acetate; Solubilizer selected from citric acid, edetic acid, polyphosphoric acid and their salts, the amount of which is 1 to 100% (w/w) of the amount of the equivalent acid of Active Ingredient; and Stabilizer selected from the group consisting of mannitol, xylitol, sorbitol, glucose, fructose, lactose and maltose, the amount of which is 50 to 200% (w/w) of the amount of the equivalent acid of Active Ingredient.

24. A method of treating or preventing sepsis in a mammal in need thereof comprising administering to said mammal a therapeutically effective amount of an aqueous solution comprising
   (a) Sodium [[3-(2-amino-1,2-dioxoethyl)-2-ethyl-1-phenylmethyl)-1H-indol-4-yl]oxy]acetate,
   (b) Trisodium Citrate Dihydrate, and
   (c) Mannitol.

* * * * *